United States Patent [19]

Ozdemir

[11] Patent Number: 4,853,543
[45] Date of Patent: Aug. 1, 1989

[54] METHOD AND APPARATUS FOR DETECTING A TRACER GAS USING A SINGLE LASER BEAM

[76] Inventor: Phillip Ozdemir, P.O. Box 69, Plainfield, N.J. 07060

[21] Appl. No.: 43,962

[22] Filed: Apr. 29, 1987

Related U.S. Application Data

[63] Continuation-in-part of Ser. No. 531,729, Sep. 13, 1983, abandoned.

[51] Int. Cl.[4] .............................................. G01N 21/33
[52] U.S. Cl. ................................. 250/372; 250/338.5; 356/51; 356/416
[58] Field of Search ...................... 250/338.5, 345, 372; 356/402, 407, 434, 438, 342, 301, 51, 416

[56] References Cited

U.S. PATENT DOCUMENTS 4,489,239 12/1984 Grant et al. ........................... 250/339

OTHER PUBLICATIONS

Edward R. Murray, "Remote Measurement of Gases Using Discretely Tunable Infrared Lasers", SPIE, vol. 95, Modern Utilization of Infrared Technology 11 (1976).
Remote Measurement of Atmospheric Mercury Using Differential Absorption Lidar, Optics Letters, vol. 7, No. 5, May 1982.
Airborne Differential Absorption Lidar System for Water Vapor Investigations, Browell & Carter, Optical Engineering, vol. 20, No. 1, Jan./Feb. 1981.
Mercury Contamination, D'Itri, John Wiley & Sons, N.Y. (1977).
Exploration of Geothermal Areas Using Mercury: A New Geochemical Technique, Matlick & Buseck, Govt. Printing Office (1976).
Mercury Vapor as a Guide to Lead-Zinc-Silver Deposits, Hawkes and Williston, Mining Congress Journal, pp. 30-32, Dec. 1962.

*Primary Examiner*—Carolyn E. Fields
*Assistant Examiner*—John A. Miller
*Attorney, Agent, or Firm*—Cushman, Darby & Cushman

[57] ABSTRACT

A method and apparatus for airborne prospecting for base and precious metal deposits, petroleum and natural gas deposits, geothermal steam deposits, and leaks in natural gas pipelines. A trace gas associated with the deposits in the near-surface atmosphere is detected with a differential absorption optical technique utilizing only a single laser beam to perform remote differential optical measurement. Anomalies in the tracer gas, which are indicative of underground deposits, are detected by transmiting a laser beam having narrow linewidth laser pulses at a high repetition rate with a center wavelength approximately equal to the atomic absorption line of the tracer gas to the area under investigation. The pulses are directed toward the investigated area from an airborne platform, reflected off the ground, and are collected by a detector on the airborne platform. Each pulse received is then broken down into a portion containing energy which is coincident with the absorption line of the tracer gas and a portion which is non-coincident with the absorption line of the tracer gas using a special optical filter. A tracer gas cell removes all the energy from the pulse which is coincident with the tracer gas absorpotion line, and the energy detected from the tracer gas cell corresponds to the amount of energy in the pulse which is off-resonance. By subtracting the off-resonance energy from the total energy received, it is possible to calculate the energy in the pulse which is received in the on-resonance spectral interval.

35 Claims, 6 Drawing Sheets

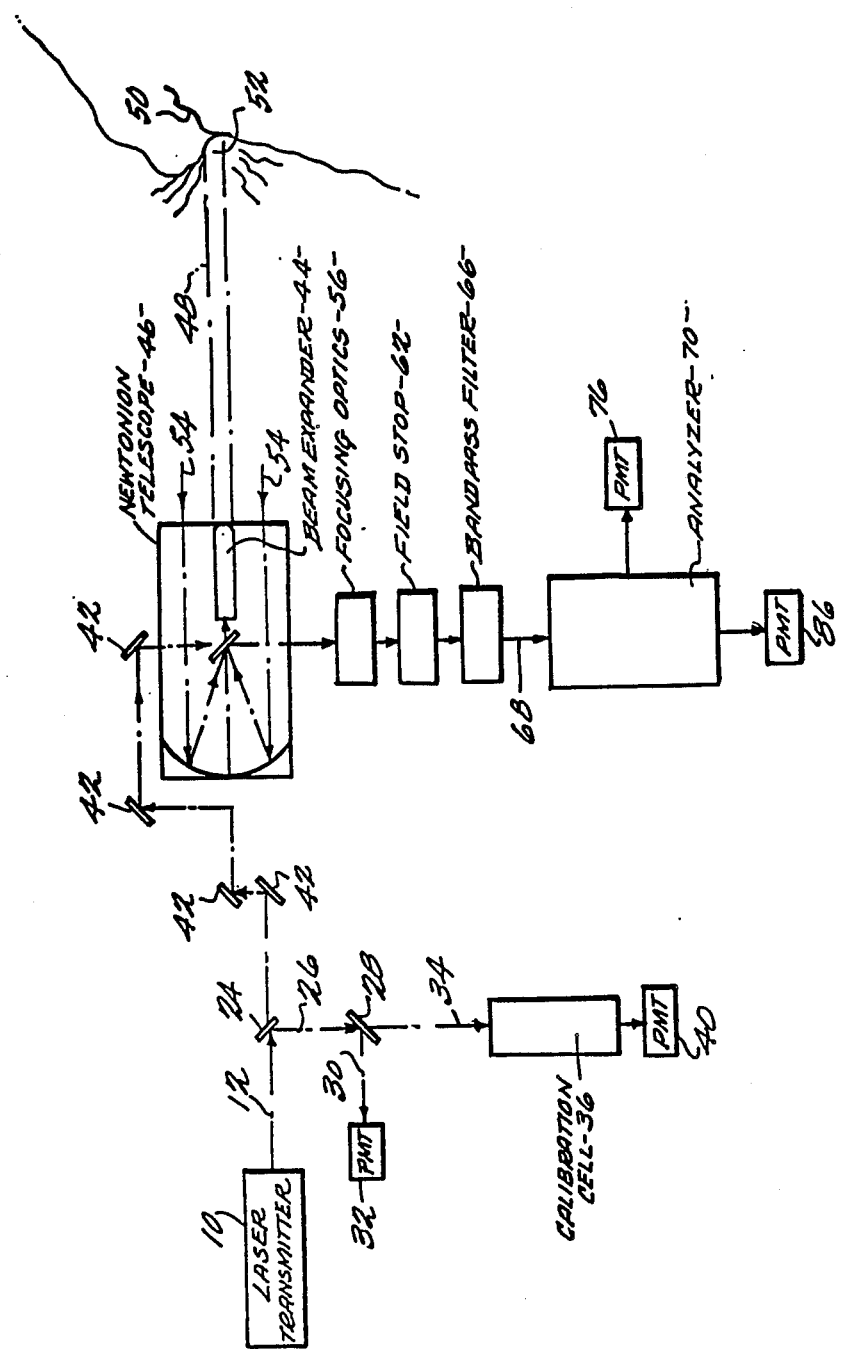
F I G. 2

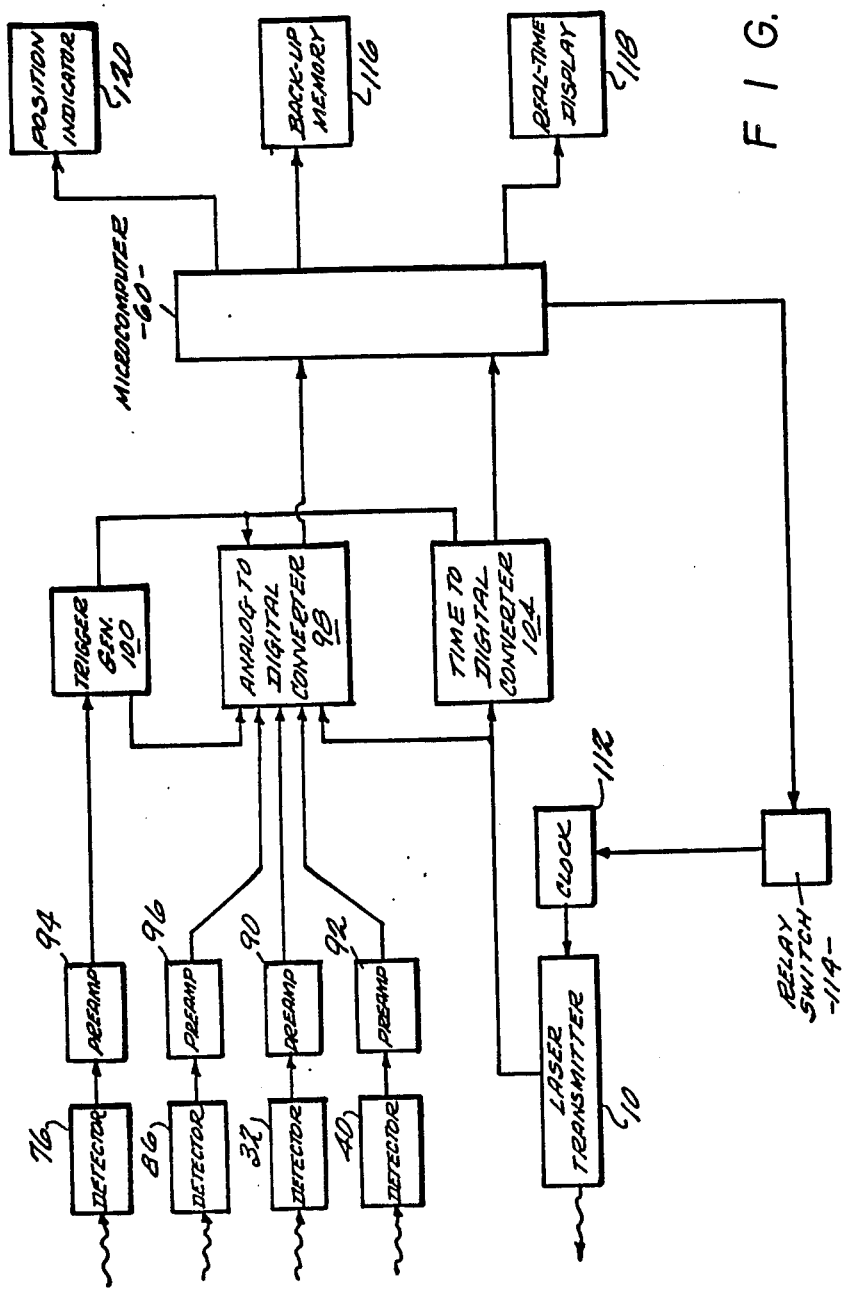

METHOD AND APPARATUS FOR DETECTING A TRACER GAS USING A SINGLE LASER BEAM

CROSS-REFERENCE TO RELATED APPLICATIONS

This application is a continuation-in-part of application Ser. No. 531,729, filed Sept. 13, 1983 abandoned, entitled "Differential Absorption Laser Prospecting", the contents of which are hereby incorporated by reference.

BACKGROUND OF THE INVENTION

1. Field of the Invention

The present invention relates to detecting a tracer gas in the near-surface atmosphere. More specifically, the present invention relates to a system for remotely locating mineral deposits, petroleum and natural gas deposits, geothermal steam deposits and leaks in natural gas pipelines by detecting a tracer gas using a single laser beam.

2. Description of the Prior Art

In the early stages of man's quest for natural gas and petroleum, almost all drilling for underground deposits followed a pattern of selecting drill sites by the proximity to oil and gas seeps which could be perceived without the aid of any equipment. Soon, however, deposits causing these visible seeps became exhausted, and those who wished to prospect for petroleum had to begin to rely on other methods. Over the past century, other techniques have been discovered and developed employing, for example, the refraction seismograph, the reflection seismograph, the magnetometer, and the gravameter. Together with geological analysis, the use of these geophysical tools has helped the prospector in his seemingly impossible task of locating with some degree of accuracy an underground deposit.

Without any direct surface indication, however, such indirect geophysical methods of prospecting are necessarily time consuming, laborious, complicated and expensive. In addition, and perhaps most importantly, these techniques have only marginally improved the exploratory drilling success ratio, i.e., the number of successful wells drilled versus the total number of wells drilled, since the period after the exhaustion of deposits associated with visible seeps and before such geophysical methods were available.

It would therefore be an enormous improvement if means were found to detect the most tenuous of seeps which have so far remained undetected in order to prospect for underground deposits. In most cases, these seeps will be located above "fault trap" types of deposits since the fault allows for a relatively easy communication of light hydrocarbon gases from the deeply buried deposit to the surface. However, undetected seeps may also be located above stratographic, anticline, reef, upward unconformity, salt dome and pinch out types of reservoirs. Obviously, they may be more easily distinguished above shallow reservoirs and over reservoirs which have a relatively porous caprock.

Numerous ground-based methods exist for measuring the concentration of hydrocarbons entrained in the soil and those which exist in the near-surface atmosphere. These methods necessitate that measurements be performed on the ground, however, in the vicinity of the seep. Surveying large amounts of land through the use of such ground-based methods is expensive and time consuming.

To overcome this problem, prospectors have developed a technique for remotely detecting light hydrocarbon molecules as they may exist emanating from the ground, indicating the presence of a deposit. Thus, for example, U.S. Pat. No. 3,651,395 to Owen et al teaches that light hydrocarbon molecules may be emanating from an underground hydrocarbon deposit. Owen et al teach the detection of the light hydrocarbon molecules through the use of their microwave re-radiation characteristics. In this scheme, target molecules are bombarded with microwave radiation that comes from a microwave transmitter on board an airborne platform. The light hydrocarbon molecules, after being struck by the microwave energy, rebroadcast at a different frequency. The particular frequency shift is characteristic of the target molecule in question. The rebroadcast radiation may then be monitored at the airborne platform.

Problems exist with this method in that it is necessary to bombard the earth's surface with microwave energy. In order for the light hydrocarbon molecules to radiate sufficient energy, a great deal of energy must be transmitted from the airborne platform. Even then, the signal received from the molecules is very weak, introducing sensitivity problems.

U.S. Pat. Nos. 4,100,481 to Gournay and 4,132,943 to Gournay et al both teach the use of microwave energy to excite gas. U.S. Pat. No. 3,351,936 to Feder also teaches the use of electromagnetic waves (either radio frequency or microwave) to explore subterranean structures. Two different radar wavelengths which have different penetration characteristics are transmitted and reflections are detected.

U.S. Pat. No. 3,741,653 to Svetlinchny teaches the use of an aircraft as a base for a laser measurement system. This system is intended only to monitor ground contours and not to detect the presence or location of particular materials. However, the remote detection of gases employing lasers is taught in Murray, "Remote Measurement of Gases Using Discretely Tuneable Infrared Lasers" in *Proceedings of the Society of Photo-Optical Instrumentation Engineers*, Vol. 95, pp. 96–104 (1976). This article teaches the projection of two laser beams having different frequencies through a remotely located sample chamber. Radiation reflected from a topical feature is detected, and the differential amount of absorption between the two laser beams is employed as an indication of the concentration of the sample gas in the remotely located chamber.

U.S. Pat. Nos. 3,861,809 to Hall and 3,807,876 to Nakahara both teach the measurement of the amount of absorption of light of a particular frequency to determine the concentrations of particular gases.

It is known to those skilled in the art that trace gases having spectral absorption characteristics in the ultraviolet range can be detected remotely, during prospecting, through the use of differential absorption laser radar (DIAL) techniques. Ahmed et al, "Remote Monitoring of Gaseous Pollutants by Differential Absorption Laser Techniques", Environmental Protection Agency, EPA-600/2-80-049, for example, teaches the remote detection of sulphur dioxide and nitrogen dioxide in the ultraviolet spectral region. In addition, Alden et al, "Remote Measurement of Atmospheric Mercury Using Differential Absorption Lidar", Optics Letters, Vol. 7, No. 5, May 1982 teaches the remote detection of sulphur dioxide and nitrogen dioxide in the ultraviolet spectral region. Also, Alden et al teach the remote detection of atmospheric mercury using differential absorption laser radar. Browell et al, in "Airborne Differential Absorption Lidar System For Water Vapor Investigations", Optical Engineering, January/February 1981, Vol. 20, No. 1, pp. 84–90, teach the use of DIAL to detect water vapor. However, the disadvantages of these techniques stem from the fact that two separate laser beams must be used to perform the differential absorption measurement.

Using two separate laser beams to perform the differential absorption measurement severely limits the sensitivity of the measurement. It is also known to those skilled in the art that during each measurement, the turbulent effects of the atmosphere play a role in degrading the measurement sensitivity. As taught by Killinger and Menyuk, "Remote Probing of the Atmosphere Using a $CO_2$ DIAL System", IEEE J. Quant. Elect. Vol. QE-17, No. 9, September 1981, introducing a distinct time delay between the time of travel of one laser pulse with respect to the time of travel of another laser pulse will increase the statistical noise of the measurement. Thus, the sensitivity achievable using this technique is limited, and such a time delay between the two laser pulses is necessary when operating a single laser differential absorption lidar (DIAL Lidar) in the "sequential" mode due to the recovery time of (the laser the laser can not fire fast enough).

As disclosed in U.S. patent application Ser. No. 531,729, now abandoned, a DIAL Lidar can also operate in the "simultaneous" mode. In this mode, two physically separate laser beams are sent out simultaneously. Thus, there is no time delay between them. However, this mode is generally not feasible for gases having their absorption spectra in the ultraviolet because of the difficulty of manufacturing spectral bandpass filters which will allow one but not both of the beams to pass through. Furthermore, even if the problem of manufacturing sufficiently workable bandpass filters could be solved, thus providing a means to discriminate between the two beams when they return to the measurement platform, there is still a disadvantage in operating with two physically separate laser beams in the ultraviolet in the "simultaneous" mode. When operating in either the sequential or the simultaneous mode, for example, beam pointing errors degrade the measurement. This effect is caused by the fact that the two pulses may propagate through slightly different beam paths and reflect off slightly different sections of the ground. Thus, the difference in their measured intensities may be due to other factors rather than due to the presence of the tracer gas in the atmosphere.

The use of two laser beams also constitutes a serious practical disadvantage because the apparatus necessary to perform the measurement has to consist of two physically separate laser systems. The cost of two laser systems is a serious disadvantage. In the case of operation in the simultaneous mode, the apparatus has to consist of two physically separate laser systems in order to be able to generate the two different wavelengths simultaneously. In the case of operation in the sequential mode, on the other hand, the apparatus may also consist of two separate laser systems because of the need to fire over time intervals very much smaller than existing laser repetition rates will allow one to fire over because of the need to minimize the measurement error associated with changes in intensity due to a turbulent atmosphere.

Thus, it is desirable for the time interval between pulses to be very small, which heretofore has been impossible with a single laser because of the inability to fire a single laser fast enough (on time frames less than 100 microseconds).

Canadian Pat. No. 808,760 to Bradley et al teaches a DIAL technique employing a single laser simultaneously producing two narrow-band frequencies. However it is difficult to achieve flexibility in selecting the frequencies produced and to control the relative power levels at the two frequencies.

It is also known to those skilled in the art that hydrocarbon deposits, mineral deposits, and geothermal steam deposits can be located through the use of mercury vapor anomalies. These anomalies occur in the soil gas and in the near-surface atmosphere. As taught in the article to Kartsev, the mercury vapor anomalies may indicate the presence of a buried petroleum or natural gas deposit because mercury as an atom in the environment often becomes absorbed into organic materials in sedimentary basins, and the element often becomes associated with petroleum and natural gas in buried pools. Furthermore, as taught by D'Itri and D'Itri, Mercury Contamination: A Human Tragedy, Wiley & Sons, New York (1977), up to 1.4 million pounds per year of mercury are released into the atmosphere from the burning of fossil fuels such as coal, oil, and natural gas. Accordingly, discoveries of high concentrations of mercury vapor are often indicative of the presence of an oil or gas deposit, since mercury is trapped in the supergene enrichment process by recycling into carboniferous precursor beds.

Also, it is known to those skilled in the art that deposits of precious and base metals may be detected through the use of mercury vapor anomalies in the soil gas and in the near-surface atmosphere. Hawkes and Williston, "Mercury Vapor as a Guide to Lead-Zinc-Silver Deposits", Mining Cong. J., December 1962, for example, teaches that patterns of mercury vapor may exist above concealed mineral deposits which can be used as exploration targets in the search for ore bodies. It is also known to those skilled in the art that geothermal steam deposits can be located with the aid of mercury vapor soil gas surveys. Matlick and Buseck, "Exploration for Geothermal Areas Using Mercury: A New Geochemical Technique", Proc. Second U.N. Geotherm, Symp., Govt. Printing Office (1976), for example, teaches the advantages of this mercury vapor technique in prospecting for geothermal deposits.

Thus, there is a need for a method and apparatus to overcome the limitations of having to use two physically separate laser beams to make a DIAL lidar measurement in order to locate a tracer gas such as mercury vapor in the ultraviolet range such that petroleum and natural gas, geothermal steam, and precious and base metals deposits can be located. A better method and apparatus is also needed for locating the presence of leaks in natural gas pipelines from a remote location, for while the presence of leaks somewhere in the line can be ascertained by a measured pressure drop, locating the leak exactly is much more problematical.

SUMMARY OF THE INVENTION

The purpose of the present invention is to overcome the disadvantages noted above in prior art atmogeochemical prospecting devices by eliminating the need for the use of two lasers or the sequencing of laser pulses in a differential absorption technique.

This purpose is accomplished in the present invention by using a laser transmitter which provides high-power, laser pulses at a high repetition rate with a bandwidth including the resonant frequency of the tracer gas but being broader than the resonance of the gas. The pulses are then directed toward the area under investigation for the tracer gas. In most cases, the apparatus will be carried aboard an airborne platform, and the area of investigation will be the area beneath the aircraft as it moves along the flight path. The pulses travel down through the atmosphere, reflect off the ground, and then are collected back onboard the aircraft by means of a large aperture telescope.

Each pulse has a portion of its energy coincident with the absorption line of the tracer gas and a portion which is non-coincident. As each pulse returns to the aircraft, it is broken down into these component portions by means of a special optical filter or "analyzer". The analyzer consists of a beam splitter, two photodetectors, and a filter which may consist of an optical cell containing a saturated volume of the tracer gas. The beam splitter splits the received pulse into two physical parts. The first part goes directly to a photodetector which measures the total power or energy contained in the pulse. The second part passes through the tracer gas cell and then impinges on the other photodetector which measures the energy or power falling on it. Since the tracer gas cell will remove all the energy from the pulse which is coincident with the tracer gas absorption line, the only energy the second photodetector will measure is that amount of energy in the pulse which is "off-resonance". By subtracting the off-resonance energy from the total energy received, it is possible to calculate the energy in the pulse which was received in the "on-resonance" spectral interval.

The present invention then takes these detected on-resonance and off-resonance values and compares them with the known values of the on-resonance and off-resonance energies which were first sent out by the transmitter. The concentration of the tracer gas in the atmospheric path of the light pulse is then calculated in a processing unit continuously as the airborne platform upon which the present invention is placed flies over various terrains. In this manner, it can be determined whether or not any anomalous concentrations of the tracer gas exist in the near-surface atmosphere. If any such anomalous concentrations are found, they are correlated with the existence of underground mineral or hydrocarbon deposits or with the presence of a leak in a natural gas pipeline.

The present invention may be used as a first-stage exploration tool with discovered anomalies verified later by geophysical or other means, or it may be used as a corroborating tool itself, verifying what electromagnetic pulse or other exploration means may have identified. Accordingly, the method and apparatus of the present invention represents an improvement over the previous techniques for atmogeochemical prospecting for underground deposits in that it uses only a single ultraviolet laser beam to effect a remote quantitative measurement of a tracer gas such as mercury vapor in the exterior atmosphere.

BRIEF DESCRIPTION OF THE DRAWINGS

These and other objects and advantages of the present invention will become more apparent and more readily appreciated from the following description of the presently preferred exemplary embodiments thereof, taken in conjunction with the accompanying drawings, of which:

FIG. 2 is an optical schematic of the presently preferred embodiment of the present invention;

FIG. 6 is an electronic schematic of the laser transmitter, receiver and processor portions of the presently preferred embodiment of the present invention.

DETAILED DESCRIPTION OF THE PRESENTLY PREFERRED EMBODIMENT OF THE INVENTION

Figure 5A:
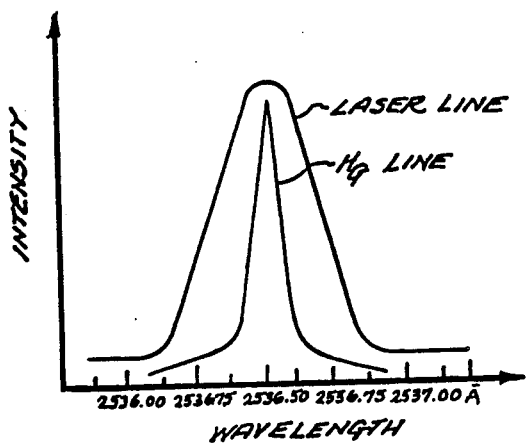
FIGS. 5A and 5B are graphical representations of the return measurement beam before and after passing through a mercury analyzer and the associated spectral absorption line of mercury.

As noted in the background of the invention, mercury vapor has been used as a pathfinder gas for locating underground deposits of petroleum, natural gas, geothermal steam, and precious and base metals. Mercury vapor is a particularly good pathfinder gas because it has a differential absorption spectra with a very sharp transition as shown in FIG. 5a. This is so because the differential absorption of the mercury gas is caused by an atomic transition and not a molecular transition in response to the incident light. As also shown in FIG. 5a, the incident light is more readily absorbed at the frequency corresponding to the atomic absorption line of mercury, which occurs at 2536.50 Angstroms. Accordingly, the present invention will be described below with reference to mercury vapor as a tracer gas. However, as will be apparent to one skilled in the art, detection of other tracer gases using the disclosed method and apparatus is within the scope of the present invention.

Figure 1:
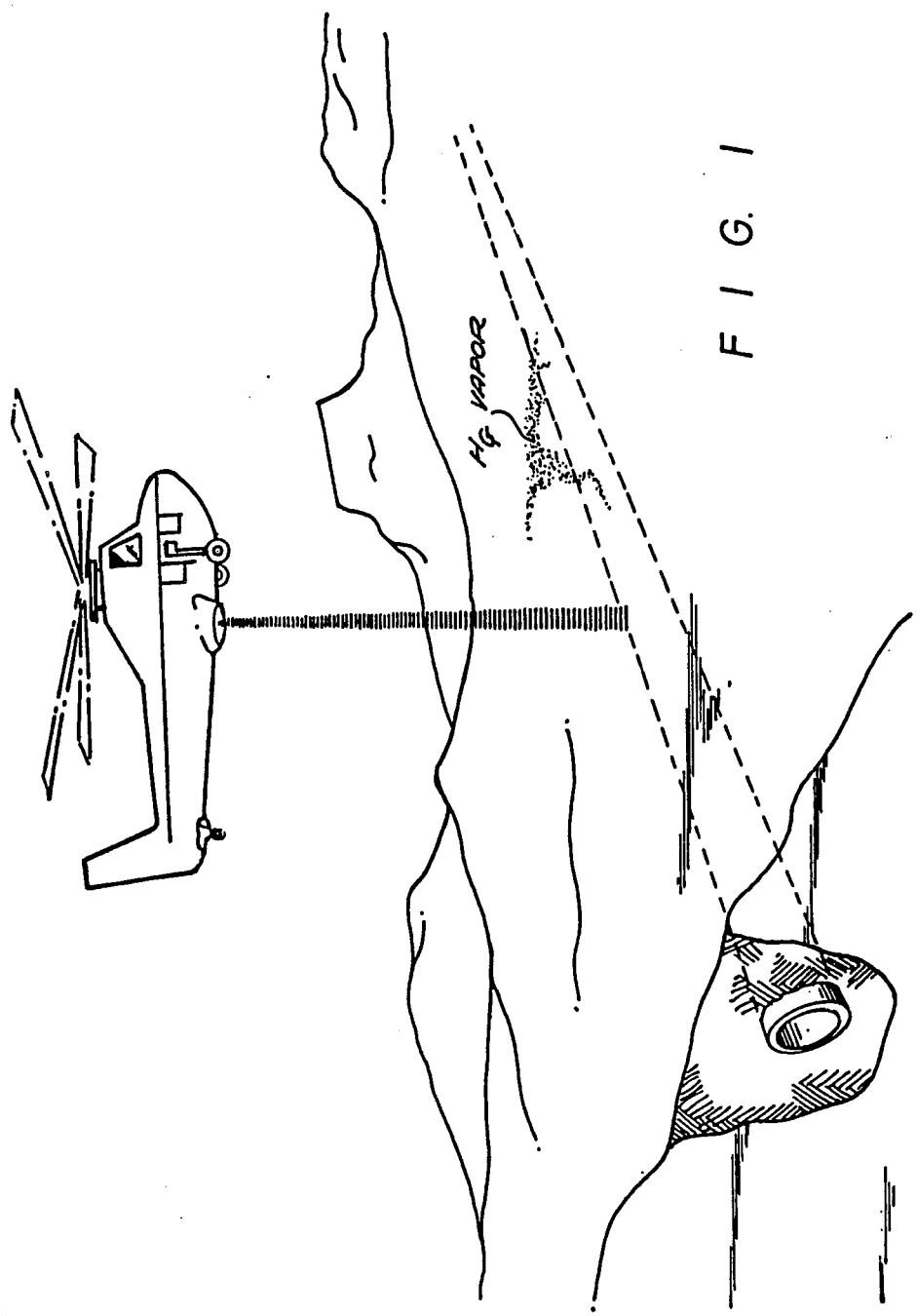
FIG. 1 is a schematic of the operation of the present invention for detecting a natural gas pipeline leak.

It is not generally known that leaks in pipelines can be located by detecting mercury vapor anomalies in the soil gas and near-surface atmosphere above buried natural gas transmission and distribution lines. There is no known use of this technique in the industry. However, the present inventor has discovered that mercury is present in the natural gas being transmitted through the transmission lines because the contamination is originally present in the gas when it gets pumped out of the ground, and chemical "scrubbing" does little to remove it. The mercury vapor thus travels along with the commercial gas and escapes along with it if there is a leak in the pipeline. Generally, mercury vapor is highly absorbed by the iron in the pipeline walls; however, there are measurable quantities of mercury vapor in the pipeline hundreds of miles from the original field, thus rendering the mercury vapor soil gas or near-surface atmospheric technique a highly viable one for detecting leaks in pipelines. Such a technique is generally shown in FIG. 1, in which the apparatus of the present invention is mounted on an airborne platform on a helicopter which flies over the buried natural gas pipeline being checked for leaks.

Turning now to FIG. 2, the optical schematic of the means for generating the laser beam and detecting the reflected laser radiation for such purposes are shown. The apparatus of the present invention consists of a laser transmitter 10 which generates a specific bandwidth, high-powered pulse of radiation 12 centered at the atomic absorption line of the tracer gas. As noted above, by way of example, it will be assumed for purposes of the present description that the tracer gas is mercury vapor having an absorption line centered at 2536.5 Angstroms. Accordingly, in the preferred embodiment, laser transmitter 10 transmits pulses of high powered laser radiation 12 centered at 2536.5 Angstroms.

Figure 3:
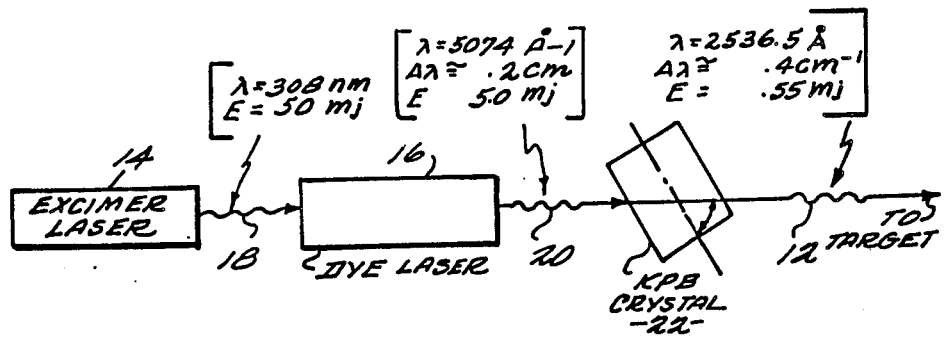
FIG. 3 is a detail of the laser transmitter portion of the embodiment of FIG. 2 showing the method used to generate laser radiation at 2536.5 Angstroms when mercury vapor is used as a tracer gas.

As shown in FIG. 3, in the preferred embodiment, the laser transmitter consists of an excimer laser 14 which pumps a dye laser 16. Such lasers are readily available. For example, the excimer laser may be a Lambda Physik Model EMG-53MSC excimer laser, and the dye laser may be a Lambda Physik Model FL2002e dye laser. The excimer laser outputs light 18 into dye laser 16 which is then pumped up so as to output light 20. Dye laser output 20 then pumps a potassium pentaborate optical crystal 22 which doubles the frequency of the dye laser light output to 2536.5 Angstroms; however, a Raman cell or other similar device may also be used to double the frequency of the dye laser output. The laser transmitter is capable of pulsing at a rate of 200 Hz with approximately 0.5 millijoule of output energy in a 0.05 cm-1 cm spectral width. For purposes of the present invention, it is desirable for the spectral width of the laser transmitter output to be centered at the atomic absorption line of the tracer gas and to have a spectral bandwidth greater than that of the tracer gas. Such limitations can be met using the laser transmitter apparatus shown in FIG. 3 for a tracer gas such as mercury vapor.

Referring back to FIG. 2, the outputted laser light 12 is split into two portions before it is projected toward the target. Beam splitter 24 taps off a small portion 26 of the beam after it emerges from laser transmitter 10. This small portion, representing a sampling of approximately 5%, of the total pulse energy, is used for reference purposes. It is then split into two parts by beam splitter 28, each part of which represents approximately 50% of the total sampled portion. Sampled portion 30 is directed toward photodetector 32 which measures the total sampled pulse energy. Sampled portion 34, on the other hand, is directed through a calibration cell 36 which contains a known concentration of the tracer gas (mercury vapor) maintained at a fixed temperature. The temperature of the mercury vapor is fixed by use of a temperature stabilization mechanism (not shown).

Calibration cell 36 is of a precise length and is used to determine the effective molecular absorption coefficient for each laser pulse so as to determine the effective absorption cross-section for the mercury vapor. Calibration cell 36 removes part of the energy in the reference pulse which is coincident with the absorption line of mercury. This provides a means of determining the linewidth of each outgoing pulse 12 as well as determining the center frequency of each outgoing pulse 12. Pulse energy 38 outputted by calibration cell 36 is then measured by photodetector 40.

Photodetectors 32 and 40 may be of any commercially available type, such as pyroelectric, photoconductive, or photovoltaic detectors, or they may be photomultiplying tubes. These detectors may be cryogenically cooled, thermoelectrically cooled or they may be at room temperature.

Beamsteering mirrors 42 are used to direct the main portion of the beam emerging from transmitter 10 to beam expanding telescope 44 which is mounted collinearly with the receiving telescope 46. The beam is then expanded to increase the beam size to a practical diameter for efficient prospecting in pipeline leakage control or atmogeochemical prospecting. The width of the beam is governed by the amount of interference which the system may tolerate. For example, if the beam is spread out too far, too much outside interference may be detected; however, if the beam is too narrow, it may be extremely difficult to cover a very large prospecting area with the beam in a given time interval. Once the desired beam width is chosen, beam 48 is projected down to the surface of the earth. On its way to the surface, and after it has reflected off topographical target 50, the beam may encounter mercury vapor 52 in the atmosphere. An amount of the light radiation is absorbed by mercury vapor 52, the amount depending upon the amount of mercury vapor present.

After the beam has reflected off topographical target 50 and propagated back to the airborne platform, return beam 54 collected by large aperture Dobsonian Newtonian reflecting telescope 46. Focusing optics 56 ensure that the beam is properly focused. Field stop 62 ensures that the radiation which passes further into the receiver is spatially coincident with the projected cone of radiation from the laser transmitter. After passing through field stop 62, the detected radiation impinges on bandpass filter 66 which removes all stray radiation outside the preferred spectral region. In the preferred embodiment, bandpass filter may be, for example, an Oriel Model 56400 Mercury Line Interference Filter which has a 110 Angstrom FWHM bandwidth and a transmission of 20% at the center wavelength of 2536.5 angstroms.

Figure 4:
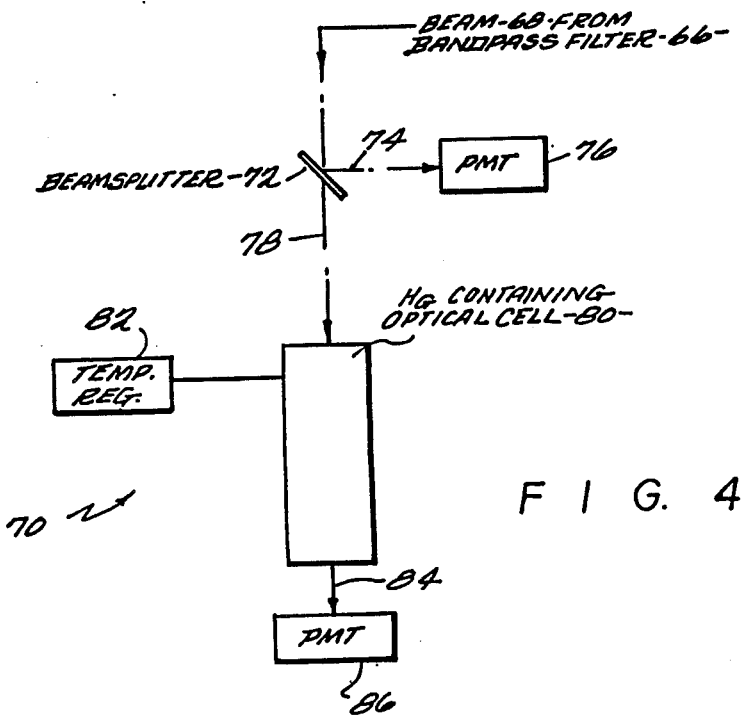
FIG. 4 is a detail of the analyzer of the embodiment of FIG. 2 used to break down the received radiation into its on-resonance and off-resonance portions.

Outputted beam 68 then enters analyzer 70, which can be seen in more detail with reference to FIG. 4. As shown in FIG. 4, analyzer 70 contains a beam splitter 72 which splits the detected radiation into two parts. The first part 74 is detected by photodetector (photomultiplying tube) 76. The second part 78 passes through an optical cell 80 containing a saturated volume of the tracer gas (mercury vapor) at a regulated temperature. The temperature of the cell is regulated by a temperature regulation mechanism 82. The temperature of the near-surface atmosphere being targeted may be determined by a remote temperature sensor (not shown) which relays the temperature to the temperature regulating mechanism for adjustment. In the absence of such a temperature adjustment mechanism, the temperature of the cell may be kept at a temperature which is judged to approximate the average temperature of the area under investigation. It is important that the temperature of the mercury vapor in the optical cell be regulated and kept at the temperature of the area under investigation because of the wide fluctuation its absorption cross-section can have with temperature.

Figure 5B:
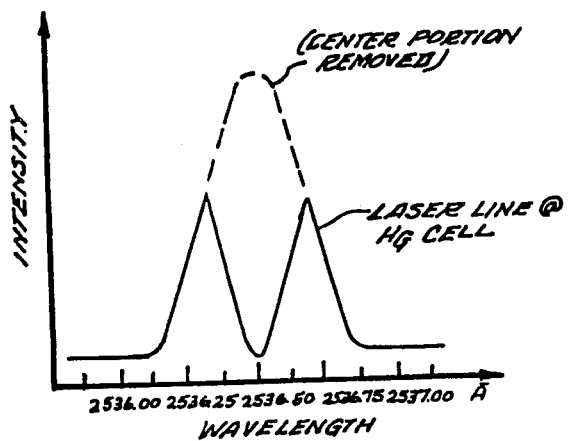

The effect of optical cell 80 is to absorb all of the optical energy in the central spectral portion of the beam coinciding with the optical absorption line of mercury. Thus, the only energy which passes through optical cell 80 is that which is contained in the "wings", or regions of the beam's spectrum which are on either side of the mercury absorption line. The intensity of beam 84 after it passes through optical cell 80 is detected by photodetector (photomultiplying tube) 86. As shown in FIG. 5B, the portion of the detected energy centered at the mercury absorption line is removed by optical filter 80. In the preferred embodiment of the present invention, photodetectors 76 and 86 may be Thorn EMI Model 6818QB photomultiplying tubes which have a very high responsivity in this wavelength region.

Referring now to FIG. 6, a schematic of the receiving and control electronics of a single beam mercury vapor LIDAR prospecting system in accordance with the preferred embodiment of the present invention is shown.

As shown, the signals outputted by photodetectors 32 and 40 associated with calibration cell 36 are preamplified by preamplifiers 90 and 92, and the signals outputted by the photomultiplying tubes 76 and 86 are preamplified by preamplifiers 94 and 96, respectively. The output of preamplifiers 90-96 are then digitized by analog to digital converter 98. In the preferred embodiment, analog-to-digital converter 98 may be a LeCroy Research 2249 SG Separately Gated ADC with a charge integrating feature. The ADC channel gates for analog-to-digital converter 98 are opened by trigger generator 100 which functions as a discriminator and a gate generator. A control signal from trigger generator 100 causes the appropriate channel of converter 98 to accept data from preamplifiers 90-96 and convert it to digital form.

A particular type of discriminator used in the preferred embodiment of trigger generator 100 is a threshold level discriminator, but in general, any type of discriminator may be used to establish the detection of the light pulse by detectors 76 or 86 including zero-crossing discriminator and signal rise time discriminators. In addition, a peak sensing analog-to-digital converter may be employed. In fact, the discriminator may be replaced with an external altimeter to open the appropriate channel of converter 98 after a preselected delay from the laser firing corresponding to the detected altitude.

The preferred gate generator for trigger generator 100 is the LeCroy Model 2323 Dual Gate and Delay Generator which, upon command from the discriminator, supplies a 100 nanosecond gating pulse on line 102 to analog-to-digital converter 98. Trigger generator 100 is informed of the fact that the light pulses have returned to the measurement platform by the presence of signal current in preamplifier circuit 94 (preamplifier circuit 96 may also be used), the presence of which is detected by trigger generator 100.

As well as providing gate signals for the analog-to-digital converter 98, trigger generator 100 supplies a signal to a time-to-digital converter (TDC) 104 to tell it to stop counting. In the preferred embodiment, time-to-digital converter 104 may be a LeCroy Model 4201 Time to Digital Converter. Time-to-digital converter 104 is employed to measure the time of flight of the transmitted laser pulse in order to measure the distance to a topographical target. This distance measurement is supplied to microcomputer 60.

Synchronization of the present invention is controlled by clock 112. In response to a signal from microcomputer 60, switch relay unit 114 causes clock 112 to begin producing signals. In response to the signal from clock 112, laser transmitter 10 fires. Included within laser transmitter 10 is another clock which generates sync pulses which are applied to analog-to-digital converter 98 to cause appropriate channels to open to cause data from preamplifiers 90 and 92 to be converted into digital form. Also, as is clear to those skilled in the art, laser transmitter 10 need not have an internal clock. Instead, an external clock or any other timing mechanism may be employed to control the firing sequence of the laser and the opening of channels in analog-to-digital converter 98.

Signals indicating the firing of laser transmitter 10 are also applied to time-to-digital converter 104. As noted above, this unit is employed to generate an indication of the distance the laser beam travels between generation and detection. Upon receipt of the firing signal from laser transmitter 10, converter 104 begins counting. When trigger generator 100 receives an indication that laser radiation has been received by detector 76, trigger generator 100 generates a control signal on line 102 to cause the counter in time-to-digital converter 104 to stop counting. The count stored in converter 104 is a measure of the round-trip travel time of the laser radiation and is immediately transformable into the distance that the beam travels upon multiplication by the speed of light.

Data converted by analog-to-digital converter 98 is applied to microcomputer 60 along with the distance data generated by time-to-digital converter 104. The intensities of the two different spectral portions of the received beam digitized by the analog-to-digital converter 98 are then analyzed by microcomputer 60 together with the measured intensities of the transmitted laser pulse 12. Microcomputer 60 calculates the concentration of the mercury vapor in the target area by using the following equation:

$$N_{atmos} = \frac{N_{cell} \cdot L \cdot \ln(P/P')}{2 \cdot R \cdot \ln(Pc/Pc')}$$

where:
$N_{atmos}$ = Concentration of mercury vapor in atmosphere in parts per billion,
$N_{cell}$ = Concentration of mercury vapor in calibration cell 36 in parts per billion,
L = Length of calibration cell 36 in meters,
P = Intensity of received radiation, on-resonance, in watts,
P' = Intensity of received radiation, off-resonance, in watts,
R = Distance to target in meters,
$P_{cI}$ = intensity of transmitted radiation, on-resonance, in watts and,
$P_c'$ = Intensity of transmitted radiation off-resonance in watts.

It should also be noted that the total power transmitted and received (as detected by detectors 32 and 76, respectively) minus the power "in the wings" (as detected by detectors 40 and 86, respectively) is equal to the power at the on-resonance frequency. Detectors 40 and 86, of course, indicate off-resonance power transmitted and received respectively, directly. All of this raw measurement data (including position data to be described below) is stored in digital form in backup memory 116.

Microcomputer 60 calculates the concentration of the target gas for each laser pulse and then shows the measured concentration in real-time on display 118, which may be, in the preferred embodiment, a Princeton Graphics Model SR 12 high-resolution CRT monitor. Also, microcomputer 60 receives position information from position indicator 120, which feeds coordinates to microcomputer 60 for determining the position of the differential absorption measurement, either with respect to fixed ground stations, or known satellite positions. At present, satellite positioning systems are limited by the fact that they do not give measurements in real-time 100 percent of the time. However, further advances in the state of the art are expected to change this soon so that precise, real time position information will be available all of the time.

There are many readily commercially available radio positioning systems which are applicable for giving a position of an aircraft. These are, in general, much more accurate than simple navigational aids such as LORAN-C; therefore, the measurement is fixed much more precisely over the ground. The readily commercially available radio positioning systems applicable to the present invention operate in the microwave or radio portion of the spectrum. Some are limited to line of sight measurement (approximately 80 kilometers at 1.0 kilometer altitude), but others are not. In addition to using the radio positioning system on board which reads out the position of the plane in real-time, it is also possible, in accordance with the general principles of the invention, to calculate the aircraft's position by the principle of "dead reckoning", i.e., using the knowledge of the speed of the aircraft and the time between each laser measurement. In a preferred embodiment of the present invention, however, position indicator 120 may be a Texas Instruments Model TI4100 Navstar Global Positioning System. The output of this navigation receiver is then stored along with the mercury vapor concentration data calculated for that point in memory device 116 for later processing. In a preferred embodiment, memory device 116 is a Kennedy Model 6455 Cartridge Tape Drive.

Instead of measuring the time of travel of the laser beam with time-to-digital converter 104, alternate approaches may be taken in order to determine an indication of the distance traveled to determine the target gas concentration. Thus, if an airborne platform is used for the laser and detectors, an external altimeter (either of the barometric or microwave variety) may be used. In fact, a fixed distance may be employed representing the average diameter of a cloud of target gas. This approach recognizes the fact that target gas from a gas seep will remain close to the surface of the earth and not be distributed evenly over the path between the laser and the point of reflection.

Figure 7:
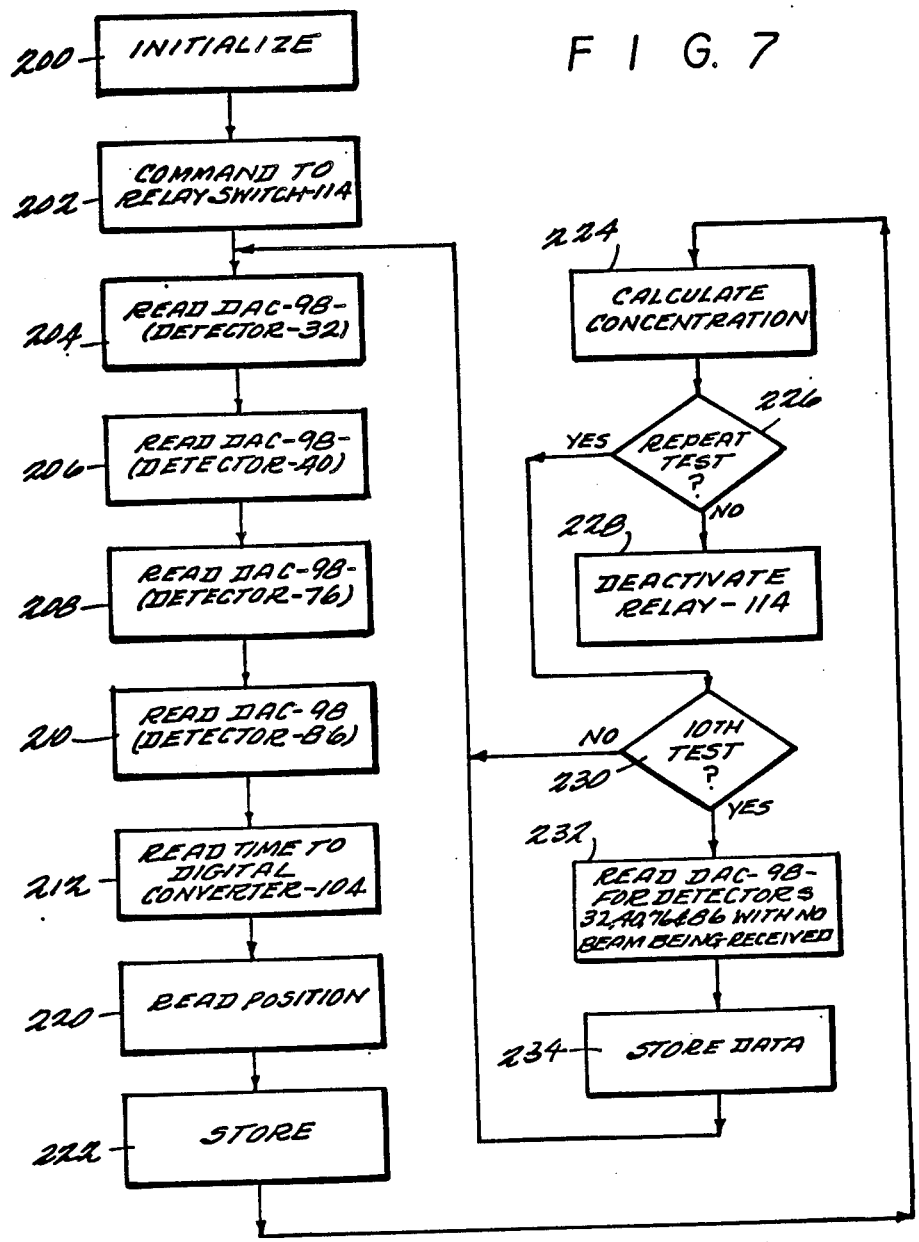
FIG. 7 is a flow diagram of the program employed in the microcomputer shown in FIG. 6.

The manner in which the preferred embodiment operates will now be described with reference to FIG. 7, which shows a flow chart of the operations performed by microcomputer 60. At the beginning of the measurement cycle, after initialization step 200, microcomputer 60, at step 202, generates a command for relay switch 114 to begin a laser firing sequence. As a result, switch 114 instructs laser transmitter 10, with its built-in clock, to begin a laser firing sequence. As a result, laser transmitter 10 fires and immediately sends a signal to analog-to-digital converter 98 to cause it to sequentially convert data from detectors 32 and 34 via preamplifiers 90 and 92, respectively. At steps 204 and 206, microcomputer 60 sequentially reads this data from converter 98. At the same time, a signal from laser transmitter 10 also causes time-to-digital converter 104 to begin counting.

Radiation 12 from laser transmitter 10 is transmitted toward the area under investigation. Eventually, that beam is reflected and detected by detector 76. This data is received by trigger generator 100, which then produces a signal 102 transmitted to both analog-to-digital converter 98 and time-to-digital converter 104. The output signal to converter 104 from trigger generator 100 causes converter 98 to process data from detectors 76 and 86. The output signal 102 to time-to-digital converter 104 causes the counter within converter 104 to stop counting. Then, at steps 208 and 210, microcomputer 60 reads the data from detectors 76 and 86 which has been converted by analog-to-digital converter 98. Finally, at step 212, microcomputer 60 reads the count stored in time-to-digital converter 104 as an indication of the distance the laser beam traveled.

At step 220, microcomputer 60 reads the position at which the measurement was taken from position indicator 120. At step 222, all of the raw data that has been collected from detectors 32, 40, 76 and 86, time-to-digital converter 104, and position indicator 120 are stored in backup memory 116 as a single record. Then, at step 224 the concentration of the target gas is calculated using Equation 1 and all of the data that has been collected, the concentration then being displayed on real-time display 118.

This concludes the basic measurement cycle. However, in the preferred embodiment, it is typical that the cycle should be continuously repeated. At some point, however, the test will be stopped. At step 226, microcomputer 60 determines whether a command has been received to indicate that the test should be stopped. If it is to be stopped, at step 228, a signal is generated to deactivate relay switch 114.

If the test is to be repeated, control passes to step 230, at which it is determined whether the tenth test has just been performed. If it has not, processing returns to step 204, at which time clock 112 causes the firing sequence to be repeated. Obviously, microcomputer 60 must be synchronized roughly with clock 112 and the clock within laser transmitter 10.

If the test which has just been completed is the tenth test as determined by step 230, microcomputer 60 instructs analog-to-digital converter 98 to sequentially process data from detectors 32, 40, 76 and 86 with no laser radiation being received at step 232. This procedure allows for measurement of preamplifier drift. This drift is stored continuously with every tenth cycle, and the results are stored in backup memory 116 step 234 and is useful in later error analysis. Control then returns to step 204.

It is advantageous to employ as high a test repetition rate as possible. When several laser measurements are performed over the same spot on the ground, the specially-resolved concentration measurements can be increased in accuracy. This increase, which is brought about by averaging the back-scattered laser shots, is found to be proportional to the square root of the number of times that the measurement is repeated. The increase in accuracy which results from averaging over several laser shots is due to the effect of averaging out large scale atmospheric fluctuations which affect statistically the propagation of the laser beam.

The present invention, utilizing the above-described apparatus, is able to resolve target concentrations down to 1.0 parts per billion in a one meter optical path from a range of about 400 feet. The concentrations of atmogeochemical anomalies vary, but many are in the range of 1 to 1000 parts per billion in the first meter or so of atmosphere. Thus, the present invention represents an important tool for atmogeochemical prospecting.

The foregoing description of the presently preferred exemplary embodiment has been directed to petroleum and natural gas prospecting in which mercury vapors are detected. However, as noted at the outset, it should be understood that the general principles of the invention may be used in prospecting for other minerals as well, since many mineral deposits are associated with significant quantities of a known target gas at the surface immediately above their underground location or with characteristic contaminants in the surface soil. These gases or contaminants can originate from chemical reactions, for instance, of the mineral ore with water, or the gases or contaminants can result from radioactive reactions.

Utilizing the absorption spectrum of the target molecule, the present invention can be employed to detect the location of the associated mineral deposits. Detections of such gases are possible as long as the on/off resonance wavelengths are close enough together to fit within the spectral region defined by a laser beam with a spectral region centered about the frequency coinciding with the absorption line of the target gas and as long as the laser light includes the on/off resonance wavelengths of the target gas without being too weak to be used for prospecting. Accordingly, detection of other such target gases is within the scope of the present invention.

Although only a few exemplary embodiments of this invention have been described in detail above, those skilled in the art will readily appreciate the many modifications that are possible in the exemplary embodiment without materially departing from the novel teachings and the advantages of the invention. Accordingly, all such modifications are intended to be included within the scope of the invention as defined in the following claims.

What is claimed is:

1. A method of detecting a target gas having a predetermined atomic absorption line, comprising the steps of:
   generating a beam of laser radiation having a spectral bandwidth including, while being broader than, said predetermined atomic absorption line of said target gas;
   transmitting said beam of laser radiation toward an area to be investigated for said target gas;
   splitting the beam reflected from said area into first and second portions, said first portion including the radiation in said reflected beam in the spectral region coinciding with said predetermined atomic absorption line as an on-resonance beam, and said second portion including only the radiation in said reflected beam in the spectral region outside of said spectral region coinciding with said predetermined atomic absorption line as an off-resonance beam;
   measuring the intensities of said on-resonance beam and said off-resonance beam and producing an on-resonance energy signal and an off-resonance energy signal, respectively related thereto; and
   determining the absolute concentration of the target gas in said area from the measured intensities.

2. A method as in claim 1, wherein said target gas is mercury (Hg).

3. A method as in claim 1, wherein said laser radiation is in the ultraviolet spectral region.

4. A method as in claim 1, wherein said generating step includes the steps of:
   pumping a dye laser with an excimer laser; and
   doubling the frequency of the dye laser light to coincide with said predetermined atomic absorption line of said target gas.

5. A method as in claim 1, including the further steps of:
   tapping off a portion of the generated beam of laser radiation as a reference laser beam;
   splitting the reference laser beam into two approximately equal portions;
   measuring the total pulse energy in one portion of said reference laser beam;
   removing part of the energy in the other portion of said reference laser beam which is coincident with the predetermined atomic absorption line of said target gas in a calibration cell; and
   measuring the pulse energy remaining in the other portion of said reference laser beam after it has passed through said calibration cell.

6. A method as in claim 5, wherein said calibration cell contains a known quantity of said target gas for determining the effective absorption cross-section of said target gas.

7. A method as in claim 5, wherein said reflected beam splitting step includes the steps of:
   splitting the reflected beam into two portions;
   measuring the pulse energy of one portion of said reflected beam;
   passing the other portion of said reflected beam through an optical cell containing a saturated volume of said target gas at a regulated temperature, said optical cell absorbing the optical energy in the other portion of said reflected beam which is coincident with the predetermined atomic absorption line of said target gas;
   measuring the pulse energy remaining in the other portion of said reflected beam after it has passed through said optical cell as said off-resonance energy signal; and
   subtracting said off-resonance energy signal from the measured pulse energy of said one portion of said reflected beam to get said on-resonance energy signal.

8. A method as in claim 7, wherein said target gas concentration determining step includes the steps of:
   generating an indication of the distance said transmitted laser beam travels; and
   determining the target gas concentration $N_{atmos}$ in accordance with the following equation:

$$N_{atmos} = \frac{N_{cell} \cdot L \cdot \ln(P/P')}{2 \cdot R \cdot \ln(Pc/Pc')}$$

where:
$N_{atmos}$ = Concentration of detected target gas in parts per billion,
$N_{cell}$ = Concentration of target gas in calibration cell in parts per billion,
L = Length of calibration cell in meters,
R = Distance to area being investigated for target gas,
P = Received power of on-resonance energy signal in watts,
$P'$ = Received power of off-resonance energy signal in watts,
Pc = On-resonance power of said reference laser beam in watts, and
$Pc'$ = Off-resonance power of said reference laser beam from said calibration cell in watts.

9. A method as in claim 8, wherein said distance indication generating step includes the steps of:
   measuring the time between transmitting said laser beam and measuring said reflected laser beam; and relating said time to distance.

10. A method as in claim 1, including the further step of monitoring the position of said area being investigated.

11. A method as in claim 10, including the further step of storing data related to the concentration of said target gas and the position at which said concentration was measured.

12. A method as in claim 1, including the further step of displaying in real time the concentration of said target gas.

13. A method as in claim 1, including the further step of correlating the magnitude of the concentration of said target gas detected with the existence of one of precious metals deposits, petroleum and natural gas deposits, geothermal steam deposits, and leaks in natural gas pipelines.

14. A method as in claim 1, wherein said steps are performed aboard an airborne platform.

15. A method of locating an underground deposit by detecting the presence of mercury gas, comprising the steps of:
   (a) generating a beam of ultraviolet laser radiation having a spectral region about a center frequency which coincides with an atomic absorption line of the mercury (Hg) atom;
   (b) transmitting said beam of laser radiation toward an area being investigated for the presence of mercury gas;
   (c) measuring the intensity of the transmitted laser beam;
   (d) detecting said beam of laser radiation after it has been reflected from said area;
   (e) splitting the detected beam into first and second portions;
   (f) measuring the pulse energy of said first portion of the detected beam;
   (g) passing said second portion of the detected beam through a mercury vapor-filled optical cell, said optical cell being kept at a regulated temperature, and said mercury vapor in said optical cell absorbing the optical energy in said second portion of the detected beam which is coincident with the atomic absorption line of mercury;
   (h) measuring the pulse energy remaining in said second portion of the detected beam after it has passed through said optical cell as an off-resonance energy signal;
   (i) subtracting said off-resonance energy signal from the measured pulse energy of said first portion of the detected beam to get an on-resonance energy signal;
   (j) measuring the intensities of said on-resonance energy signal and said off-resonance energy signal;
   (k) generating an indication of the distance said transmitted laser beam travels to said area;
   (l) determining the concentration of said mercury gas in said area employing the results of steps (c), (j) and (k);
   (m) relating said mercury gas concentration to the existence of said underground deposit;
   (n) displaying said mercury gas concentration in real time;
   (o) determining the position of said area being investigated; and
   (p) storing said mercury gas concentration with the position at which said mercury gas concentration was measured.

16. A method as in claim 15, wherein said steps (a) through (p) are performed aboard an airborne platform.

17. An apparatus for detecting a target gas having a predetermined atomic absorption line, comprising:
   means for generating a beam of laser radiation having a spectral bandwidth including, while being broader than, said predetermined atomic absorption line of said target gas;
   means, responsive to said generating means, for transmitting said beam of laser radiation toward an area to be investigated for said target gas;
   means for splitting said beam after it has been reflected from said area into first and second portions, said first portion including the radiation in said reflected beam in the spectral region coinciding with said predetermined atomic absorption line as an on-resonance beam, and said second portion including only the radiation in said reflected beam in the spectral region outside of said spectral region coinciding with said predetermined atomic absorption line as an off-resonance beam; and
   processing means, responsive to said first and second portions of said reflected beam, for measuring the intensities of said on-resonance beam and said off-resonance beam and for determining the absolute concentration of the target gas in said area from the measured intensities.

18. An apparatus according to claim 17, wherein said generating means generates radiation having a spectral bandwidth including the atomic absorption line of mercury (Hg).

19. An apparatus according claim 17, wherein said generating means generates laser radiation in the ultraviolet spectral region.

20. An apparatus according to claim 17, wherein said generating means comprises:
   an excimer laser;
   a dye laser which is pumped by said excimer laser; and
   frequency doubling means for doubling the frequency of the dye laser output to coincide with said predetermined atomic absorption line of said target gas.

21. An apparatus according to claim 20, wherein said frequency doubling means includes a potassium pentaborate crystal.

22. An apparatus according to claim 20, wherein said frequency doubling means includes a Raman cell.

23. An apparatus according to claim 17, further comprising calibration means for determining the intensity of the transmitted laser beam, said calibration means comprising:
   means for tapping off a portion of the generated beam of laser radiation as a reference laser beam;
   means for splitting the reference laser beam into two approximately equal portions;
   means for measuring the total pulse energy in one portion of said reference laser beam;
   a calibration cell for removing a portion of the energy in the other portion of said reference laser beam which is coincident with the predetermined atomic absorption line of said target gas; and means for measuring the pulse energy remaining in the other portion of said reference laser beam after it has passed through said calibration cell.

24. An apparatus according to claim 23, wherein said calibration cell contains a known quantity of said target gas for determining the effective absorption cross-section of said target gas.

25. An apparatus according to claim 23, wherein said means for splitting the reflected beam comprises:
filtering means containing a saturated volume of said target gas at a regulated temperature for absorbing the optical energy in one portion of said detected beam which is coincident with the predetermined atomic absorption line of said target gas; and said processing means comprises:
means for measuring the total pulse energy of the other portion of said reflected beam, and
means for measuring the pulse energy remaining of said one portion of said reflected beam after it has passed through said filtering means.

26. An apparatus according to claim 25, wherein said filtering means includes a mercury vapor-filled optical cell and said target gas is mercury (Hg).

27. An apparatus according to claim 25, wherein said processing means includes:
means for generating a value related to the distance between said transmitting means and said area; and
means for determining the target gas concentration $N_{atmos}$ in accordance with the following equation:

$$N_{atmos} = \frac{N_{cell} \cdot L \cdot \ln(P/P')}{2 \cdot R \cdot \ln(Pc/Pc')}$$

where:
$N_{atmos}$ = Concentration of detected target gas in parts per billion,
$N_{cell}$ = Concentration of target gas in calibration cell in parts per billion,
L = Length of calibration cell in meters,
R = Distance to area being investigated for target gas,
P = Received power of on-resonance energy signal in watts,
P' = Received power of off-resonance energy signal in watts,
Pc = On-resonance power of said reference laser beam in watts, and
Pc' = Off-resonance power of said reference laser beam from said calibration cell in watts.

28. An apparatus according to claim 17, further comprising means for monitoring the position of said area being investigated.

29. An apparatus according to claim 28, wherein said position monitoring means includes a navigation receiver.

30. An apparatus according to claim 28, further comprising means for storing data related to the concentration of said target gas and the position at which said concentration was measured.

31. An apparatus according to claim 17, further comprising means for displaying in real time the concentration of said target gas.

32. An apparatus according to claim 17, further comprising means for detecting said beam of laser radiation after it has been reflected, said detecting means comprising:
a detector for receiving said reflected laser beam;
trigger generating means, coupled to said detector, for sensing the reception of a reflected laser beam; and
analog-to-digital converting means, coupled to said detector and said trigger generating means, for converting the output of said detector in response to an indication from said trigger generating means.

33. An apparatus according to claim 17, further comprising an airborne platform on which said generating means, transmitting means and splitting means are disposed.

34. An apparatus for locating an underground deposit by detecting the presence of mercury gas, comprising:
means for generating a beam of ultraviolet laser radiation having a spectral region about a center frequency which coincides with an atomic absorption line of the mercury (Hg) atom;
means, responsive to said generating means, for transmitting said beam of laser radiation toward an area being investigated for the presence of mercury gas;
means for measuring the intensity of the transmitted laser beam;
means for detecting said beam of laser radiation after it has been reflected from said area;
means for splitting the detected beam into first and second portions;
means for measuring the pulse energy of said first portion of said detected beam;
a mercury vapor-filled optical cell kept at a regulated temperature for absorbing the optical energy in said second portion of said detected beam which is coincident with the atomic absorption line of mercury;
means for measuring the pulse energy remaining in said second portion of said detected beam after it has passed through said optical cell as an off-resonance energy signal;
processing means, responsive to said first and second portions of said detected beam, for subtracting said off-resonance energy signal from the measured pulse energy of said first portion of said detected beam to get an on-resonance energy signal; for measuring the intensities of said on-resonance energy signal and said off-resonance energy signal; for generating an indication of the distance said transmitted laser beam travels to said area; for determining the concentration of said mercury gas in said area in response to the outputs of said means for measuring the intensity of the transmitted laser beam, said means for measuring the intensities of said on-resonance energy signal and said off-resonance energy signal, and said means for generating an indication of the distance said transmitted laser beam travels to said area; and for relating said mercury gas concentration to the existence of said underground deposit;
means for displaying said mercury gas concentration in real time;
means for determining the position of said area being investigated; and
means for storing said mercury gas concentration with the position at which said mercury gas concentration was measured.

35. An apparatus according to claim 34, further comprising an airborne platform on which said generating means, transmitting means and detecting means are disposed.

* * * * *